(12) United States Patent
Sembo

(10) Patent No.: US 7,144,583 B2
(45) Date of Patent: Dec. 5, 2006

(54) PESTICIDAL COMPOSITION

(75) Inventor: Satoshi Sembo, Nishinomiya (JP)

(73) Assignee: Sumitomo Chemical Company, Limited, Osaka (JP)

( * ) Notice: Subject to any disclaimer, the term of this patent is extended or adjusted under 35 U.S.C. 154(b) by 148 days.

(21) Appl. No.: 10/770,886

(22) Filed: Feb. 3, 2004

(65) Prior Publication Data

US 2004/0176368 A1    Sep. 9, 2004

(30) Foreign Application Priority Data

Mar. 5, 2003    (JP)    ............... 2003-058130

(51) Int. Cl.
*A01N 25/00*    (2006.01)
*A01N 43/50*    (2006.01)
*A61K 31/535*    (2006.01)
*A61K 31/415*    (2006.01)

(52) U.S. Cl. ............... 424/405; 424/405; 514/229.2; 514/389

(58) Field of Classification Search ............... 514/471
See application file for complete search history.

(56) References Cited

U.S. PATENT DOCUMENTS

| | | | |
|---|---|---|---|
| 4,176,189 A | | 11/1979 | Itaya et al. |
| 5,462,938 A | | 10/1995 | Annus et al. |
| 6,218,416 B1 | * | 4/2001 | Sembo ............... 514/389 |
| 2002/0115565 A1 | * | 8/2002 | Asrar et al. ............... 504/100 |

FOREIGN PATENT DOCUMENTS

| WO | WO 01/37662 A1 | 5/2001 |
|---|---|---|
| WO | WO 02/28186 A2 | 4/2002 |
| WO | WO 03/011031 A1 | 2/2003 |

OTHER PUBLICATIONS

International Organization for Standardization (http://web.archive.org/web/20020625100627/http://www.alanwood.net/pesticides/class_insecticides.html).*

* cited by examiner

*Primary Examiner*—Alton N. Pryor
*Assistant Examiner*—David P. Stitzel
(74) *Attorney, Agent, or Firm*—Akin Gump Strauss Hauer & Feld, LLP

(57) ABSTRACT

A pesticidal composition comprising an oxadiazine compound given by formula (A):

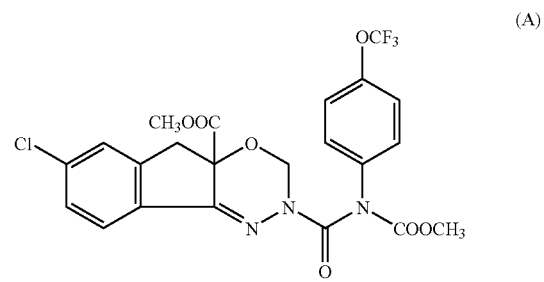

and an ester compound given by formula (B):

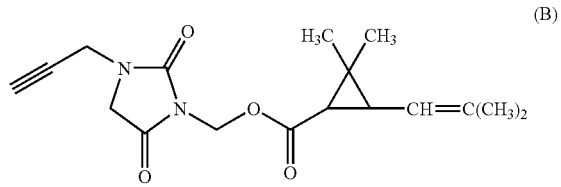

as active ingredients, wherein the weight ratio of the oxadiazine compound given by formula (A) to the ester compound given by formula (B) is within the range of 50:1 to 1:10, has an excellent efficacy for controlling pests.

9 Claims, No Drawings

PESTICIDAL COMPOSITION

FIELD OF THE INVENTION

The present invention relates to a pesticidal composition.

BACKGROUND ARTS

It is known that an oxadiazine compound given by formula (A):

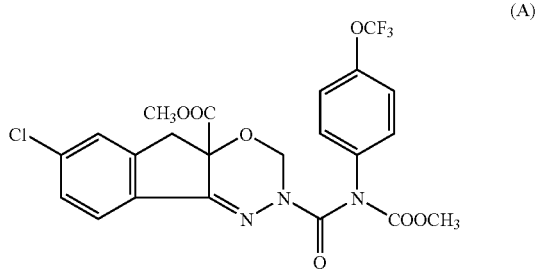

has an activity for controlling harmful arthropods in U.S. Pat. No. 5,462,938.

Further, it is also known that an ester compound given by formula (B):

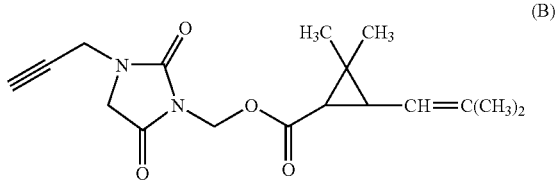

has an activity for controlling harmful arthropods in U.S. Pat. No. 4,176,189.

SUMMARY OF THE INVENTION

The present invention provides a pesticidal composition which comprises the oxadiazine compound given by formula (A) (hereinafter referred to as Compound (A)) and the ester compound given by formula (B) (hereinafter referred to as Compound (B)) as active ingredients, wherein the weight ratio of the oxadiazine compound given by formula (A) to the ester compound given by formula (B) is within the range of 50:1 to 1:10. Further, the present invention also provides a method for controlling pests which comprises applying an effective amount of Compound (A) and Compound (B) to pests or a place where the pests inhabit, wherein the weight ratio of the oxadiazine compound given by formula (A) to the ester compound given by formula (B) is within the range of 50:1 to 1:10.

DISCLOSURE OF THE INVENTION

The pesticidal composition of the present invention comprises Compound (A) and Compound (B) as active ingredients. The weight ratio of Compound (A) to Compound (B) in the pesticidal composition is 50:1 to 1:10, preferably 20:1 to 1:4. The pesticidal composition is effective for controlling various pests, and further a synergistic joint action gives decrease of an application dosage of each compound.

Compound (A), methyl 7-chloro-2,5-dihydro-2-[[(methoxycarbonyl)[4-(trifluoromethoxy)phenyl]amino]carbonyl] indeno[1,2-e][1,3,4]oxadiazine-4a(3H)carboxylate, is a compound described in U.S. Pat. No. 5,462,938, and can be prepared according to the method disclosed in the publication. Indoxacarb, methyl (S)-7-chloro-2,5-dihydro-2-[[(methoxycarbonyl)[4-(trifluoromethoxy)phenyl] amino] carbonyl]indeno[1,2-e][1,3,4]oxadiazine-4a(3H)-carboxylate, is produced by E. I. DuPont. Further, a flowable formulation of Indoxacarb MP, methyl (RS)-7-chloro-2,5-dihydro-2-[[(methoxycarbonyl)[4-(trifluoromethoxy)phenyl] amino]carbornyl]indeno[1,2-e][1,3,4]oxadiazine-4a (3H)-carboxylate, is provided by Kumiai Chemical Company (commercial name: Tornado 10FL). With regard to the absolute configuration of the asymmetric carbon in Compound (A), (S)-compound is preferable in the view of the efficacy for controlling pests. Thus, (S)-compound of Compound (A) or (S)-rich form is preferably used.

Compound (B), 2,5-dioxo-3-prop-2-ynylimidazolidin-1-ylmethyl 2,2-dimethyl-3-(2-methylprop-1-enyl)cyclopropanecarboxylate, is a compound described in U.S. Pat. No. 4,176,189, and can be prepared according to the method disclosed in the publication. Further, Imiprothrin, 2,5-dioxo-3-prop-2-ynylimidazolidin-1-ylmethyl (1R)-trans,cis-2,2-dimethyl-3-(2-methylprop-1-enyl)cyclopropanecarboxylate, is produced by Sumitomo Chemical Company. Compound (B) also has stereoisomers, and with regard to the chrysanthemic acid part of Compound (B), (1R)-isomer is preferable in the view of the efficacy for controlling pests.

Examples of the pests against which the pesticidal composition of the present invention gives controlling effect are the following harmful arthropods (e.g. insects and acarina):

Hemipteran pests: Delphacidae (planthoppers) [e.g. *Laodelphax striatellus* (small brown planthopper), *Nilaparvata lugens* (brown planthopper) and *Sogatella furcifera* (white-backed rice planthopper)], Deltocephalidae and Cicadellidae (leafhoppers) [e.g. *Nephotettix cincticeps* (green rice leafhopper) and *Nephotettix virescens* (green rice leafhopper)], Aphididae (aphids) [e.g. *Aphis gossypii* (cotton aphids) and *Myzus persicae* (green peach aphid)], Heteroptera (stink bugs) [e.g. *Nezera antennata* (green stink bug) and *Riptortus clavatus* (bean bug)], Aleyrodidae (whiteflies) [e.g. *Trialeurodes vaporariorum* (greenhouse whitefly) and *Bemisia argentifolli* (silverleaf whitefly)], scales [e.g. *Aonidiella aurantii* (California red scale), *Comstockaspis perniciosa* (San Jose scale), *Unaspis citri* (citrus snow scale), *Ceroplastes ruhens* (red wax scale) and *Icerya purchasi* (cottonycushion scale)], Tingidae (lace bugs), Psyllidae (suckers) and so on;

Lepidopteran pests: Pyralidae [e.g. *Chilo suppressalis* (rice stem borer), *Cnaphalocrocis medinalis* (rice leafroller), *Notarcha derogata* (cotton leafroller) and *Plodia interpunctella* (Indean meal moth)], Noctuidae [e.g. *Spodoptera litura* (tobacco cutworm), *Pseudaletia separata* (rice armyworm), *Trichoplusia* spp., *Heliothis* spp. and *Helicoverpa* spp.], Pieridae [e.g. *Pieris rapae crucivora*], Tortricidae [e.g. *Adoxophyes* spp., *Grapholita molesta* (oriental fruit moth) and *Cydia pomonella*], Carposinidae [e.g. *Carposina niponensis* (peach fruit moth)], Lyonetiidae [e.g. *Lyonetia* spp.], Lymantriidae [e.g. *Lymantria* spp. and *Euproctis* spp.], Yponameutidae [e.g. *Plutella xylostella* (diamondback moth)], Gelechiidae [e.g. *Pectinophora gossypiella* (pink bollworm)], Arctiidae (tiger moths) [e.g. *Hyphantria cunea* (fall webworm)], Tineidae [e.g. *Tinea translucens* (casemaking clothes moth) and *Tineola bisselliella* (webbing clothes moth)] and so on;

Dipteran Pests: *Culex* spp. [e.g. *Culex pipiens pallens* (common mosquito), *Culex tritaeniorhynchus* and *Culex quinquefasciatus*], *Aedes* spp. [*Aedes aegypti* (yellow fever mosquito) and *Aedes albopictus*], *Anopheles* spp. [e.g. *Anopheles sinensis*], Chironomidae (midges), Muscidae [e.g. *Musca domestica* (housefly) and *Muscina stabulans* (false housefly)], Calliphoridae, Sarcophagidae, *Fannia* spp. (little houseflies), Anthomyiidae [e.g. *Delia platura* (seedcorn maggot) and *Delia antique* (onion maggot)], Tephritidae (fruit flies), Drosophilidae (vinegar flies), Psychodidae (sand flies), Simuliidae (black flies), Tabanidae, Stomoxyidae (stable flies), Agromyzidae (leafminer flies) and so on;

Coleopteran Pests: corn rootworms [e.g. *Diabrotica virgifera* (western corn rootworm) and *Diabrotica undecimpunctata howardi* (southern corn rootworm)], Scarabaeidae (scarabs) [e.g. *Anomala cuprea* and *Anomala rufocuprea* (soybean beetle)], weevils [e.g. *Sitopiilus zeamais* (maize weevil), *Lissorhoptrus oryzophilus* (ricewater weevil) and *Callosobruchuys chienensis* (adzuki bean weevil)], Tenebrionidae (darkling beetles) [e.g. *Tenebrio molitor* (yellow mealworm) and *Tribolium castaneum* (red flour beetle)], Chrysomelidae (leaf beetles) [e.g. *Aulacophora femoralis* (cucurbit leaf beetle), *Phyllotreta striolata.* (striped leaf beetle) and *Leptinotarsa decemlineata* (Colorado beetle)], Anobiidae, *Epilachna* spp. [e.g. *Epilachna vigintioctopunctata* (twenty-eight-spotted ladybird)], Lyctidae (powderpost beetles), Bostrychidae, Cerambycidae, *Paederus fuscipes* (robe beetle) and so on;

Dictyopteran Pests: *Blattlla germanica* (German cockroach), *Periplaneta fuliginosa* (smokybrown cockroach), *Periplaneta americana* (American cockroach), *Periplaneta brunnea* (brown cockroach), *Blatta orientalis* (oriental cockroach) and so on;

Thysanopteran Pests: *Thrips palmi, Thrips tabaci* and so on;

Hymenopteran Pests: Formicidae (ants) [e.g. *Monomorium nipponensis* (little ant)], Vespidae (hornets), Bethylidae, Tenthredinidae (sawflies) [e.g. Athalia japonica (cabbage sawfly)] and so on;

Orthopteran pests: Gryllotalpidae (mole crickets), Acrididae (grasshoppers) and so on;

Siphonapteran pests: *Ctenocephalides felis* (cat flea), *Ctenocephalides canis* (dog flea), *Pulex irritans* (human flea), *Xenopsylla cheopis* and so on;

Anopluran pests: *Pediculus humanus corporis* (human body louse), *Phthirus pubis* (crab louse), *Haematopinus eurysternus* (cattle louse), *Dalmalinia ovis* (sheep louse) and so on;

Isopteran pests; *Reticulitermes speratus, Coptotermes formosanus* (Formosan subterranean termite) and so on; and Acarina pests; Tetranychidae (spider mites) [e.g. *Tetranychus urticae* (two-spotted spider mite), *Panonychus citri* (citrus red mite) and *Oligonychus* spp.], Eriophyidae [e.g. *Aculops pelekassi* (pink citrus rust mite)], Tarsonemidae [e.g. *Polyphagotarsonemus latus* (broad mite)], Tenuipalpidae, Tuckerellidae, Ixodidae (ticks) [e.g. *Haemaphysalis longicornis, Haemaphysalis flava, Dermacentor taiwanicus, Ixodes ovatus, Ixodes persulcatus, Boophilus microplus* and *Rhipicephalus sanguineus*], Acaridae [e.g. *Tyrophagus putrescentiae*], Dermanyssidae [e.g. *Dermatophagoides farinae* and *Dermatophagoides ptrenyssnus*], Cheyletidae [e.g. *Cheyletus eruditus, Cheyletus malaccensis* and *Cheyletus moorei*], *Dermanyssus gallinae* (chicken mite) and so on.

The pesticidal composition of the present invention may be a mixture of Compound (A) and Compound (B) itself, but usually the composition further comprises a solid carrier, liquid carrier and/or gaseous carrier, optionally surfactant and the other auxiliaries to be formulated to emulsifiable concentrates, oil solutions, dusts, granules, wettable powders, flowables, microcapsule formulations, paste formulations, foam formulations, aerosols, liquid carbon oxide solution formulations, sheet formulations, resin formulations, fogging formulations, poison baits and so on.

These formulations usually contain 0.005 to 90% by weight of the total amount of Compound (A) and Compound (B).

Examples of the solid carrier include fine powders and granules of clays such as kaolin clay, diatomaceous earth, bentonite, Fubasami clay and terra alba; synthetic hydrated silicon oxide; talc; ceramics; the other inorganic minerals such as sericite, quartz, sulfur, activated carbon, calcium carbonate and hydrated silica; and chemical fertilizers such as ammonium sulfate, ammonium phosphate, ammonium nitrate, urea and ammonium chloride.

Examples of the liquid carrier include water; alcohols such as methanol, ethanol, isopropyl alcohol, butanol, hexanol, benzyl alcohol, ethylene glycol, propylene glycol and phenoxyethanol; ketones such as acetone, methyl ethyl ketone and cyclohexanone; aromatic hydrocarbons such as toluene, xylene, ethylbenzene, dodecylbenzene, phenylxylylethane and methylnaphthalene; aliphatic hydrocarbons such as hexane, cyclohexane, kerosene and gas oil; esters such as ethyl acetate, butyl acetate, isopropyl myristate, ethyl oleate, diisopropyl adipate, diisobutyl adipate and propylene glycol monomethyl ether acetate; nitriles such as acetonitrile and isobutyronitrile; ethers such as diisopropyl ether, 1,4-dioxane, ethylene glycol dimethyl ether, diethylene glycol dimethyl ether, diethylene glycol monomethyl ether, propylene glycol monomethyl ether, dipropylene glycol monomethyl ether and 3-methoxy-3-methyl-1-butanol; acid amides such as N,N-dimethylformamide and N,N-dimethylacetamide; halogenated hydrocarbons such as dichloromethane, trichloroethane and carbon tetrachloride; sulfoxides such as dimethyl sulfoxide; propylene carbonate; and vegetable oils such as soybean oil and cotton seed oil.

Examples of the gaseous carrier include fluorocarbons, butane gas, LPG (liquefied petroleum gas), dimethyl ether and carbon dioxide.

Examples of the surfactant include nonionic surfactants such as polyoxyethylene alkyl ether, polyoxyethylene alkyl aryl ether and polyethylene glycol fatty acid ester; and anionic surfactants such as alkylsulfonic acid salt, alkylbenzenesulfonic acid salt and alkylsulfuric acid salt.

Examples of the other formulation auxiliaries include adhesive agents, dispersants, coloring agents and stabilizers, and typically gelatin, saccharides (e.g. starch, gum arabic, cellulose derivatives, alginic acid), lignin derivatives, bentonite, synthetic water-soluble polymers (e.g. polyvinyl alcohol, polyvinylpyrrolidone, polyacrylic acids, PAP (isopropyl acid phosphate), BHT (2,6-di-tert-butyl-4-methylphenol), BHA (mixture of 2-tert-butyl-4-methoxyphenol and 3-tert-butyl-4-methoxyphenol), iron oxide, titanium oxide, prussian blue, alizarin dye, azo dye and phthalocyanine dye.

The pesticidal composition of the present invention can also be prepared by mixing the formulated Compound (A) and the formulated Compound (B). Further, they may be mixed when application.

The method of the present invention for controlling pests is usually carried out by applying the composition of the present invention to pests or a place where the pests inhabit (e.g. plant, soil, indoors, animal body). Further, it is possible to apply Compound (A) or its formulation and Compound (B) or its formulation to pests or a place where the pests inhabit at the same time without mixing them at advance. In the latter case, the dosage ratio of Compound (A) to Compound (B) is 50:1 to 1:10, preferably 20:1 to 1:4 by weight.

In case of utilizing the pesticidal composition of the present invention for agricultural use, the application rate of the total amount of Compound (A) and Compound (B) is usually 1 g to 10000 g per 10000 m$^2$. When the pesticidal composition of the present invention is formulated to emulsifiable concentrates, wettable powders or flowables, they are usually diluted with water to make the concentration of the active ingredients 0.01 ppm to 10000 ppm and applied. Granules or dusts are usually applied without dilution as they are.

These formulations or dilutions can be directly applied to pests or plants such as crops to be protected from the pests, or applied to soil for controlling pests which inhabit in the soil of the cultivated land.

It is possible to apply a resin formulation of sheet or string by winding around or surrounding crops, or putting on the soil near the root.

In case of utilizing the pesticidal composition of the present invention for controlling pests inhabiting indoors (e.g. flies, mosquitoes, cockroaches), the application rate of the total amount of Compound (A) and Compound (B) is usually 0.1 mg to 1000 mg per 1 m$^2$ at treating on plane and 0.01 mg to 500 mg per 1 m$^3$ at treating in space. When the pesticidal composition of the present invention is formulated to emulsifiable concentrates, wettable powders or flowables, they are usually diluted with water to make the concentration of the active ingredients 0.1 ppm to 1000 ppm and applied. Oil solution, aerosol, fogging, poison bait or sheet formulation is applied as it is.

In case of utilizing the pesticidal composition of the present invention for controlling arthropods harmful to wood materials (e.g. termites), the pesticidal composition of the present invention is applied to the pests harmful to wood materials, a place the arthropods inhabit or the wood materials such as constructional materials. In the application, any method is utilized that paints 0.01 g/m$^2$ to 30 g/m$^2$ in general at the total amount of Compound (A) and Compound (B), sprays 0.1 g/m$^2$ to 300 g/m$^2$ in general at the total amount of Compound (A) and Compound (B), admixes 0.1 g/m$^3$ to 100 g/m$^3$ in general at the total amount of Compound (A) and Compound (B) with adhesives, which are used for producing plywood, and the like.

In case of utilizing the pesticidal composition of the present invention for controlling ectoparasites of animals (e.g. pets such as dogs and cats, farm animals such as cattle and sheep), the pesticidal composition of the present invention is applied to the animals by painting or washing. The application rate is usually 0.1 mg to 1000 mg of the total amount of Compound (A) and Compound (B) per 1 kg of the body weight of the animal.

The pesticidal composition of the present invention can be used together with the other pesticidal active ingredient and/or synergist such as PBO (piperonyl butoxide), S-421 (bis(2,3,3,3-tetrachloropropyl) ether), MGK-264 (N-(2-ethylhexyl)bicyclo[2.2.1]hept-5-ene-2,3-dicarboximide), IBTA (isobornyl thiocyanatoacetate) and N-(2-ethylhexyl)-1-isopropyl-4-methylbicyclo[2.2.2] oct-5-ene-2,3-dicarboximide.

EXAMPLES

The present invention will be explained by formulation examples and test examples in more detail below; however, the present invention is not limited to these examples.

At first, formulation examples are given, in which part means part by weight.

Formulation Example 1

Two and a half (2.5) parts of Compound (A), 2.5 parts of Compound (B), 8 parts of polyoxyethylene styryl phenyl ether, 2 parts of calcium dodecylbenzenesulfonate and 85 parts of xylene are mixed to give an emulsifiable concentrate.

Formulation Example 2

Ten parts of Compound (A), 10 parts of Compound (B), 3 parts of sodium dodecylbenzenesulfonate, 3 parts of sodium ligninsulfonate and 74 parts of diatomaceous earth are mixed and pulverized with a jet mill to give wettable powders.

Formulation Example 3

One part of Compound (A), 1 part of Compound (B), 48 parts of talc and 50 parts of clay are uniformly mixed and stirred to give dusts.

Formulation Example 4

To 10 parts of Compound (A) and 5 parts of Compound (B), 5 parts of sodium dodecylbenzenesulfonate, 30 parts of bentonite and 50 parts of clay are added and well mixed under stirring. Then, to the mixture, a suitable amount of water is added, further stirred, spherized by granulator and dried through flow to give granules.

Formulation Example 5

Five parts of polyoxyethylene styryl phenyl ether sulfate, 20 parts of 1% aqueous xanthan gum solution, 3 parts of smectite mineral and 57 parts of water are uniformly mixed, and 10 parts of Compound (A) and 5 parts of Compound (B) are added thereto and well stirred. Then, they are wet-pulverized with sand mill to give a flowable.

Formulation Example 6

One-fifth (0.2) part of Compound (A) and 0.1 part of Compound (B) are dissolved in 59.7 parts of deodorized kerosene and put into an aerosol container, which is followed by attached a valve. Then, 40 parts of liquefied petroleum gas (LPG) are charged under pressure through the valve part to give an oil-based aerosol.

Formulation Example 7

To a mixture of 0.1 part of Compound (A), 0.2 part of Compound (B), 5 parts of xylene and 5 parts of trichloroethane, 89.7 parts of deodorized kerosene are added to give an oil solution.

The following test examples show the effect of the pesticidal composition of the present invention.

Test Example 1

Two grams (2 g) of each of Indoxacarb MP and Imiprothrin are mixed with 98 g of a mixture of xylene/Sorpol SM200X (surfactant produced by Toho Chemical)=85/15 to give each formulation of Indoxacarb MP and Imiprothrin. The formulations for the following tests are produced by mixing the Indoxacarb MP formulation with the Imiprothrin formulation at the designated ratio. The formulations for the tests are diluted with water to the designated concentration to give the preparations for the test.

Triangular column shaped wooden container containing 5 male and 5 female German cockroaches (*Blattlla germanica*) therein were placed upright in the central region of cubic glass box possessing a side length of 70 cm, in which said triangular column shaped wooden container possesses an equilateral triangle base, a side length of 3.5 cm and a height of 15 cm. Into the glass box, 4.2 ml of the preparation obtained above were sprayed with a spray gun. Ten minutes after spraying, the cockroaches were transferred to a plastic container and were provided with food and water. The mortality of the cockroaches was observed 4 days thereafter. The results were given in Table 1.

TABLE 1

|  | Concentration of the preparation (% by weight) | Mortality (%) |
| --- | --- | --- |
| Indoxacarb MP + Imiprothrin | 0.5 + 0.4 | 100 |
| Indoxacarb MP | 0.5 | 25 |
| Imiprothrin | 0.4 | 0 |

Test Example 2

In a cubic glass box possessing a side length of 70 cm, 10 male and 10 female adult houseflies (*Musca domestics*) were released. Into the cubic glass box, 2.1 ml of the preparation obtained in Test example 1 were sprayed with a spray gun. Ten minutes after spraying, the houseflies were transferred to a plastic container and were provided with food and water. The mortality of the houseflies was observed 2 days thereafter. The results were given in Table 2.

TABLE 2

|  | Concentration of the preparation (% by weight) | Mortality (%) |
| --- | --- | --- |
| Indoxacarb MP + Imiprothrin | 0.4 + 0.4 | 100 |

Test Example 3

In a cubic glass box possessing a side length of 70 cm, 20 female adult common mosquitoes (*Culex pipiens pallens*) were released. Into the cubic glass box, 2.1 ml of the preparation obtained in Test example 1 were sprayed with a spray gun. Ten minutes after spraying, the mosquitoes were transferred to a plastic container and were provided with food and water. The mortality of the mosquitoes was observed one day thereafter. The results were given in Table 3.

TABLE 3

|  | Concentration of the preparation (% by weight) | Mortality (%) |
| --- | --- | --- |
| Indoxacarb MP + Imiprothrin | 0.2 + 0.2 | 100 |

Test Example 4

Ten milliliters (10 ml) of the preparation obtained in Test example 1 having a designated concentration were mixed with 200 g of sterilized soil and allowed to stand for 24 hours. The soil was transferred to a Petri dish having a diameter of 9 cm and 10 worker termites (*Coptotermes formosanus*) were released thereon. The mortality of the termites was observed 3 days thereafter. The results were given in Table 4.

TABLE 4

|  | Concentration of the preparation (% by weight) | Mortality (%) |
| --- | --- | --- |
| Indoxacarb MP + Imiprothrin | 0.5 + 0.5 | 100 |

Test Example 5

One-twentieth gram (0.05 g) of Indoxacarb MP and 0.05 g of Imiprothrin are dissolved in 49.9 g of deodorized kerosene and put into an aerosol container, which is followed by attached a valve. Then, 50 g of dimethyl ether are charged under pressure through the valve part to give an aerosol for the following test.

On the other hand, 50 g of soil were put in a plastic container having a diameter of 10 cm and a height of 4.6 cm, 10 little ants (*Monomorium nipponensis*) were released thereon. One-fifth gram (0.2 g) of the aerosol obtained above was sprayed from the point over 60 cm. After spraying, the ants were provided with food and allowed to stand for 3 days. The dead or alive of the little ants was observed thereafter, and the mortality was 100%.

What is claimed is:

1. A pesticidal composition which comprises an oxadiazine compound given by formula (A):

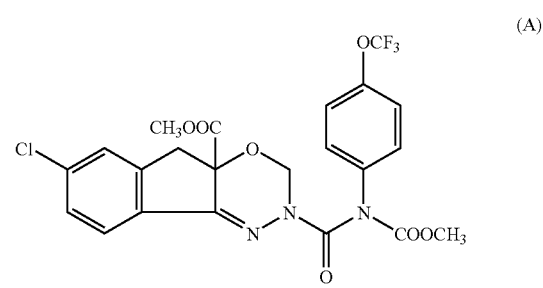

and an ester compound given by formula (B):

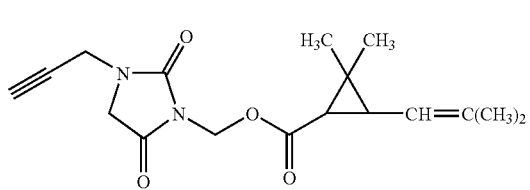

as active ingredients, wherein the weight ratio of the oxadiazine compound given by formula (A) to the ester compound given by formula (B) is within the range of 50:1 to 1:10.

2. The pesticidal composition according to claim 1, wherein the weight ratio of the oxadiazine compound given by formula (A) to the ester compound given by formula (B) is within the range of 20:1 to 1:4.

3. A method for controlling pests which comprises applying an effective amount of an oxadiazine compound given by formula (A):

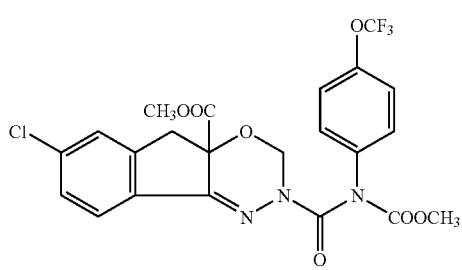

and an ester compound given by formula (B):

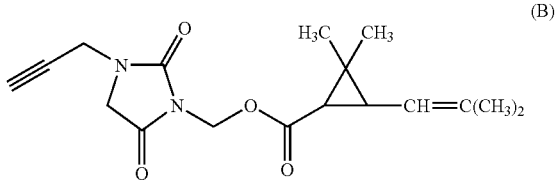

to pests or a place where the pests inhabit, wherein the weight ratio of the oxadiazine compound given by formula (A) to the ester compound given by formula (B) is within the range of 50:1 to 1:10.

4. The method for controlling pests according to claim 3, wherein the weight ratio of the oxadiazine compound given by formula (A) to the ester compound given by formula (B) is within the range of 20:1 to 1:4.

5. The method for controlling pests according to claim 3, wherein the pests are cockroaches.

6. The method for controlling pests according to claim 3, wherein the pests are flies.

7. The method for controlling pests according to claim 3, wherein the pests are mosquitoes.

8. The method for controlling pests according to claim 3, wherein the pests are termites.

9. The method for controlling pests according to claim 3, wherein the pests are ants.

* * * * *